United States Patent [19]

Strahle

[11] Patent Number: Plant 7,382

[45] Date of Patent: Nov. 20, 1990

[54] HYBRID TEA ROSE PLANT 3038-C STRAHLE CULTIVAR

[75] Inventor: Glen Strahle, Carlton, Oreg.

[73] Assignee: Carlton Rose Nurseries, Inc., Carlton, Oreg.

[21] Appl. No.: 362,082

[22] Filed: Jun. 5, 1989

[51] Int. Cl.[5] ..... A01H 5/00

[52] U.S. Cl. ..... Plt./14

[58] Field of Search ..... Plt./14

*Primary Examiner*—James R. Feyrer

*Attorney, Agent, or Firm*—Chernoff, Vilhauer, McClung & Stenzel

[57] ABSTRACT

A vigorous rose plant of the hybrid tea class obtained as a seedling from a seed parent entitled "Coquette" and a pollen parent entitled "Jack Frost" provides abundant long-lasting solid white flowers which maintain their true color from flower opening through petal drop on a continuous basis when grown in a greenhouse.

1 Drawing Sheet

BACKGROUND AND SUMMARY OF THE INVENTION

The present invention relates to a new and distinct variety of hybrid tea rose plant, a seedling resulting from a definite effort to produce an immprovement of this class of rose. The object of the present invention is to provide a rose plant of the hybrid tea class which is capable of freely yielding quality-cut flowers under greenhouse conditions.

The primary features of this new variety which connotates its distinctive advance over previously existing types is its ability to produce an abundance of overall white flowers which remain true after being cut from when they first open through petal drop from a plant which will continuously yield cut flowers under greenhouse conditions.

The variety of rose plant of the present invention was obtained at Carlton, Oreg. as a seedling from a seed parent entitled "Coquette" and a pollen parent entitled "Jack Frost". The crossing was made in 1982, the first seed of the crossing was sewn in March 1983 and the first flower appeared from these seedlings in May 1983.

Asexual reproduction of this new variety shows that its unique characteristics come true to form and is established and transmitted through succeeding propagations through grafting and budding.

BRIEF DESCRIPTION OF THE DRAWINGS

In the accompanying drawings typical specimens of the vegetative growth and flowers of the new variety are shown in different stages of development and are depicted in color as nearly true as is reasonably possible to make in color illustrations of this character.

FIG. 1 shows the inside of a petal at the top and the outside of a petal at the bottom.

FIG. 2 represents a full open flower.

FIG. 3 shows the flower at the proper stage for cutting.

FIG. 4 shows the bud as the sepals first crack.

FIG. 5 shows upper surface of a compound leaf.

FIG. 6 shows the lower surface of a compound leaf.

FIG. 7 shows the cross section of a flower with petals removed exposing the reproductive organs.

FIG. 8 shows a flower with the petals removed.

FIG. 9 shows flower with petals and stamens removed to expose the pistils.

FIG. 10 shows the hip.

FIG. 11 shows a typical stem illustrating normal branching and thorn pattern.

DETAILED DESCRIPTION OF THE DISCLOSURE

The following description was made during October 1988 of rose plants of the new and distinct variety growing in a greenhouse at Carlton, Oreg. Color designations are to *The Royal Horticultural Society Colour Chart.*

FLOWER

Flowers borne: Singly on strong, long stems.

Quantity of bloom: Abundant in greenhouse.

Continuity: Continuous.

Fragrance: Slight.

Bud:

*Peduncle.*—Medium length; medium weight; erect; light green; almost smooth; numerous hairs; yellow.

*Before calyx breaks.*—Size: medium. Form: long pointed without foliaceous appendages on the surface of the bud.

*As calyx breaks.*—Color: White Group 155-D.

*As first petal opens.*—Size: medium. Form: long pointed. Color: Outside: White Group 155-B. Inside: White Group 155-D.

Opening.—It opens up well.

Bloom:

*Size when fully open.*—Large, 3" to 5".

*Petalage.*—Very double; from 34 to 38 petals; arranged regularly. Form: high centered; petals at first being tightly cupped inward; becoming later at maturity tightly rolled outward.

Petals: Leatherly; with inside satiny; outside satiny.

*Shape.*—Outer: round. Intermediate; round. Inner: round.

*Color.*—Color of newly opened flowers: Outer petal: Outside surface: White Group 155-C. Inside surface: White Group 155-B. Intermediate petal: Outside Surface: White Group 155-A. Inside surface: White Group 155-B. Inner petal: Outside surface: White Group 155-D. Inside surface: 155-B.

*Color of flower three days after opening.*—Outer petal: Outside surface: White Group 155-D. Inner petal: Outside surface: White Group 155-D. Inside surface: White Group 155-B.

General color effect:

*Newly open flower.*—A general white color with an ivory shading toward the center of the flower.

*Flowers three days open.*—An even white color with outside petals framing center with pointed petals.

Behavior: Petals persist.

Flower longevity: Cut flowers grown in greenhouse keep at livingroom temperature 9 days during October.

REPRODUCTIVE ORGANS

Stamens: Many; arranged regularly about pistils.

*Filaments.*—Many; most with anthers; medium length.

*Color.*—Yellow.

*Anthers.*—All open at once; medium length Color: yellow. Occasionally an anther fused with a petaloid.

*Pollen.*—Abundant; gold.

*Pistils.*—Many.

*Styles.*—Uneven; medium length; medium weight; columnar.

*Stigma.*—White.

*Ovaries.*—All enclosed in receptacle.

*Hips.*—Globular; very smooth; walls thick fleshy; reddish.

*Sepals.*—Permanent; moderately long; spear-shaped, recurved.

*Seeds.*—Many; large.

PLANT

Foliage:

*Leaves.*—Compound of three five seven leaflets; moderately abundant; medium size; moderately leathery.

*Leaflets.*—Linear with apex acuminate, base round, margin simply serratedentate.

*Color.*—Mature upper surface: Green Group 139-A. Mature under surface: Green Group 138-B. Young upper surface: Green Group 137-C. Young under surface: Green Group 147-C.

*Rachis.*—Medium. Upper side: grooved. Under side: sparsely prickly.

*Stipules.*—Moderatley long; narrow; moderately short points; turning out an angle of less than 45 degrees.

*Disease.*—Resistant to mildew.

Growth:

*Habit.*—Upright.

*Growth.*—Vigorous.

*Canes.*—Moderatley heavy.

*Main stems.*—Dull. Color: Green Group 137-C. Prickles: several. Color: Greyed-orange Group 164-A. Hairs: none.

*Branches.*—Dull. Color: Green Group 137-C. Prickles: several. Color: Yellow-green Group 146-B. Hairs: none.

*New shoots.*—Dull. Color: Yellow-green Group 144-B. Prickles: several. Color: Yellow-green Group 145-B. Hairs: none.

What is claimed is:

1. A new and distinct variety of rose plant of the hybrid tea class obtained as a seedling from a seed parent entitled "Coquette" and a pollen parent entitled "Jack Frost," characterized by its overall white color which is maintained from flower opening through petal drop, and its ability to yield flowers on a continuous basis when grown in a greenhouse, substantially as shown and described.

* * * * *

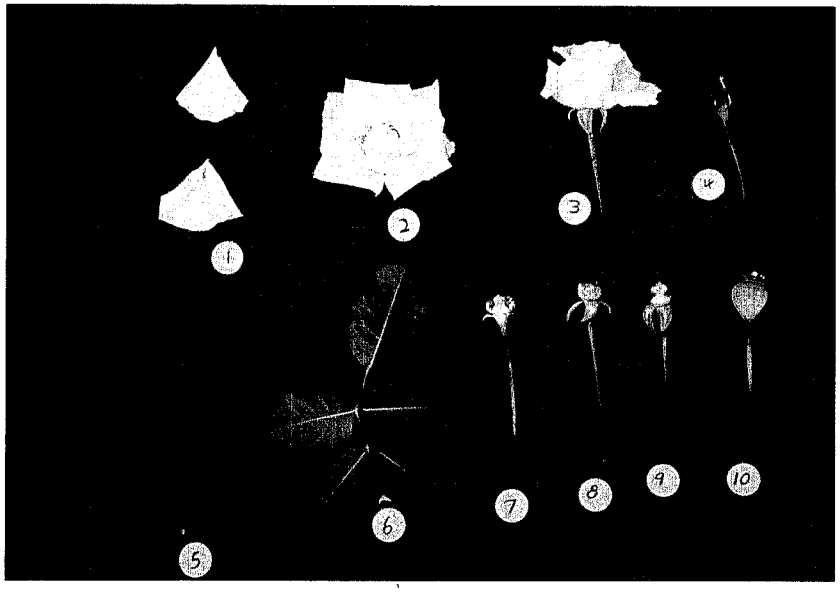
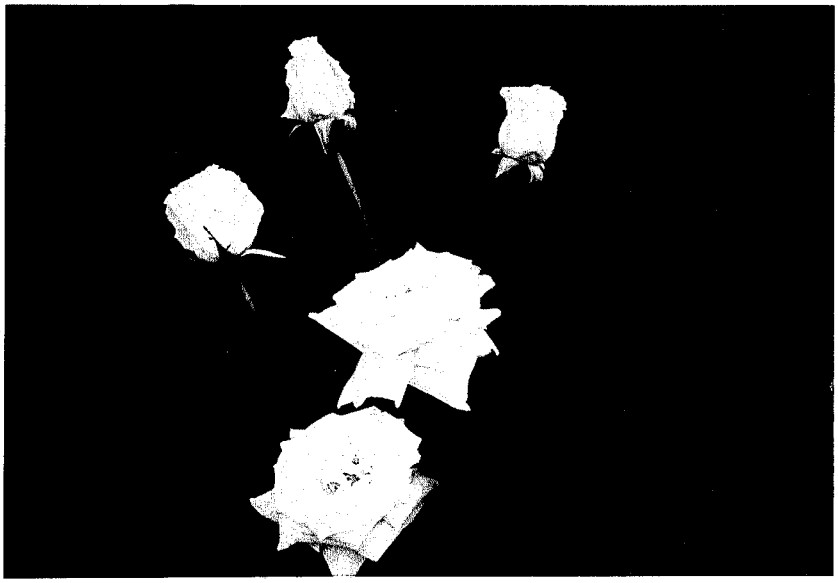
FIG. 11